US00RE42354E

(19) United States
(12) Reissued Patent
Clark

(10) Patent Number: US RE42,354 E
(45) Date of Reissued Patent: May 10, 2011

(54) HEMO-AIDE

(76) Inventor: Robert E. Clark, Lansing, MI (US)

(21) Appl. No.: 12/070,702

(22) Filed: Feb. 20, 2008

Related U.S. Patent Documents

Reissue of:
(64) Patent No.: 6,719,716
Issued: Apr. 13, 2004
Appl. No.: 10/219,656
Filed: Aug. 14, 2002

U.S. Applications:
(60) Provisional application No. 60/312,412, filed on Aug. 15, 2001.

(51) Int. Cl.
*A61M 1/36* (2006.01)
*A61L 2/00* (2006.01)

(52) U.S. Cl. ..... 604/6.08; 604/4.01; 604/28; 422/44; 250/432 R; 250/428; 250/455.11; 250/435; 250/436

(58) Field of Classification Search ..... 604/4.01, 604/5.01, 6.08
See application file for complete search history.

(56) References Cited

U.S. PATENT DOCUMENTS 3,894,236 A * 7/1975 Hazelrigg ..... 250/435
4,573,960 A * 3/1986 Goss ..... 604/6.08
4,737,140 A 4/1988 Lee et al.
5,133,932 A * 7/1992 Gunn et al. ..... 422/24
5,150,705 A * 9/1992 Stinson ..... 607/94
5,304,113 A * 4/1994 Sieber et al. ..... 604/6.08
5,429,594 A * 7/1995 Castle ..... 604/6.08
5,770,147 A * 6/1998 Muller ..... 422/24
5,951,509 A * 9/1999 Morris ..... 604/6.08
6,113,566 A * 9/2000 Schleicher ..... 604/6.08
6,951,548 B1 10/2005 Einstein
2002/0082669 A1 6/2002 Nitsch

* cited by examiner

*Primary Examiner* — Tatyana Zalukaeva
*Assistant Examiner* — Benedict L Hanrahan
(74) *Attorney, Agent, or Firm* — Knechtel, Demeur & Samlan

(57) ABSTRACT

An apparatus and method for modifying viruses and bacteria in a closed loop system that irradiates the fluid multiple times through the same channel. The apparatus consists of a cuvette, an irradiation station, a peristaltic pump, and a bottle. A plurality of power control switches controls the operation of the apparatus. This includes an on/off power switch, an on/off pump control, and a ultraviolet light control switch. A timer is provided to regulate the time period the cuvette is exposed to the ultraviolet radiation within the irradiation station. A cover is provided to enable the cuvette to be used and exposed to ultraviolet radiation within an enclosed environment.

15 Claims, 2 Drawing Sheets

HEMO-AIDE

Matter enclosed in heavy brackets [ ] appears in the original patent but forms no part of this reissue specification; matter printed in italics indicates the additions made by reissue.

*CROSS-REFERENCE TO RELATED APPLICATION*

*This patent application is a non-provisional application claiming priority from U.S. Provisional Application Ser. No. 60/312,412, entitled "Hemo-Aide" filed on Aug. 15, 2001, and is fully incorporated herein by reference.*

FIELD OF THE INVENTION

The present invention relates to the ultra violet irradiation of blood apparatus and, more particularly, to the modification of viruses and bacteria in the body without contamination using a unique method and cuvette apparatus.

BACKGROUND AND DESCRIPTION OF THE PRIOR ART

In the past, others have attempted to eradicate viruses and bacteria using a mercury vapor lamp and an irradiation chamber. This combination, however, presented a number of problems. Since the mercury vapor lamp is made with contaminating materials, the irradiation chamber could become contaminated. As a result, this type of lamp has been restricted by the Federal Drug Administration from use in the treatment of fluids in this manner. Also, as the irradiation chamber is permanently secured to the unit, sterilization of the chamber is a very difficult, time consuming task.

In an attempt to overcome this problem, a number of patents have been issued that disclose apparatus and methods for the irradiation of blood or bodily fluids. As listed below in the order of issuance, these are:

| Inventor | Issued | Title of Patent | U.S. Pat. No. |
|---|---|---|---|
| Morris | Sep. 14, 1999 | Blood Product Irradiation Device Incorporating Agitation | 5,951,509 |
| Muller | Jun. 23, 1998 | Apparatus For The Irradiation Of Body Fluids By Ultraviolet light | 5,770,147 |
| Castle | Jul. 04, 1995 | Extra-Corporeal Blood Access, Sensing And Radiation Methods And Apparatuses | 5,429,594 |
| Sieber | Apr. 19, 1994 | Method Of Eradicating Infectious Biological Contaminants | 5,304,113 |
| Stinson | Sep. 29, 1992 | Apparatus And Method For Irradiating Cells | 5,150,705 |
| Gunn | Jul. 28, 1992 | Blood Processing Apparatus | 5,133,932 |
| Goss | Mar. 04, 1986 | Three Phase Irradiation Treatment Process | 4,573,960 |
| Hazelrigg | Jul. 08, 1975 | Device For Irradiating Fluids | 3,894,236 |

Of these patents, the most relevant are: U.S. Pat. No. 5,770,147 to Muller entitled "Apparatus For The Irradiation of Body Fluids By Ultraviolet Light" ("Muller"); U.S. Pat. No. 5,429,594 to Castle entitled "Extra-Corporeal Blood Access, Sensing, and Radiation Methods And Apparatus" ("Castle"); U.S. Pat. No. 5,304,113 to Sieber entitled "Method of Eradicating Infectious Biological Contaminants" ("Sieber"); and U.S. Pat. No. 5,951,509 to Morris entitled "Blood Product Irradiation Device Incorporating Agitation" ("Morris").

Muller ('147) discloses an apparatus for the irradiation of body fluids by ultraviolet light in a containment. In one embodiment, the containment consists of a cuvette, an adaptor, a drive motor, and a Ultraviolet lamp. The cuvette, upon being filled with blood removed from a patient, is fitted into the containment and engaged with the adaptor. The cuvette is then rotated by the drive motor and exposed to the Ultraviolet radiation uniformly. The cuvette also includes flow baffles to provide additional turbulence to generate a radial flow of the blood towards the Ultraviolet radiation. Upon completion of the radiation, the cuvette is disengaged from the containment, the irradiated blood is removed from the cuvette, and then returned to the patient.

Castle ('594) discloses a method and apparatus for extra corporeal access to blood for analysis and treatment of the blood. In use, the apparatus pumps blood from a patient through an outlet line and then returns the blood back to the patient through an inlet line. During this extra corporeal flow of the blood, the outlet line and the inlet line each have access ports in which the blood may be either analyzed or treated. Any treatment of the blood consists of energy or radiation and includes ultrasonic waves.

Sieber ('113) discloses a method to erradicate infectious biological contaminants such as the human immunodeficiency virus. The method consists of withdrawing the blood from a patient using a pump, adding anti-coagulants to the blood, an occluded vein sensor to prevent or inhibit the generation or existence of bubbles in the flow of the blood, inserting a photosensitizing agent, an irradiation chamber which consists of visible light to activate the photosensitive agent, and then returning the erradicated blood to the patient.

Morris ('509) discloses an apparatus for treating human blood by irradiation. In use, blood is withdrawn from a patient and supplemented by an anti-coagulant solution. The blood is then separated into two portions by a cell separator, such as a centrifuge, with one portion being directed into a bag for irradiation and another portion either being held in storage or returned to the patient. Upon a predetermined volume of blood accumulated into the bag, the bag is placed within an irradiation apparatus. The irradiation apparatus consists of an upper lamp array and a lower lamp array of ultraviolet individual lamps and the bag is placed in the middle of the upper lamp array and the lower lamp array to irradiate the blood prior to being returned to the patient.

The combination of the above patents reveals that there exist several ways to irradiate blood from a patient. Among the common disclosure of these patents is that blood is removed from a patient, the blood is irradiated using ultraviolet light to kill contaminants and viruses, and the irradiated blood is then returned to the patient. Each patent is distinguishable in that it introduces additional steps during this process and/or accomplishes the process in a different manner. However, none of the patents disclose or teach a closed system with the ability to remove contaminated blood from a patient in one channel, effectively irradiate the blood twice using the same cuvette, and then return the irradiated blood back to the patient using the same channel, thereby, providing an effective modification of the viruses and bacteria in the blood in an attempt to eradicate the same. Thus, there is a need and there has never been disclosed an apparatus and method that solves the problems presented by today's devices and is as effective as Applicant's unique invention.

OBJECTS OF THE INVENTION

It is the primary object of the present invention to modify viruses and bacteria in the body in an attempt to eradicate the same. A related object of the present invention is to effectively modify the viruses and bacteria using a minimal number of modalities or processes. Another related object of the present invention is to have a positive impact on the condition. A further related object of the present invention is to reduce the blood count or PCR within the body.

Another object of the invention is to provide an apparatus that uses pure safe ultraviolet light and that is calibrated to the required or desired frequencies. A related object of the invention is to use the ultraviolet light for the irradiation of the blood.

Another object of the invention is to eliminate the contamination through the use of personal cuvettes. A related object of the invention is to provide a cuvette which is smaller and more compact making it suitable as a portable unit for patients who are unable to attend or fulfill scheduled appointments at hospitals, outpatient health care clinics, etc . . .

Another object of the invention is to provide an apparatus and system that is inexpensive to manufacture. A related object of the invention is to provide a system that is safe and easy to use.

Other objects of the present invention will become more apparent to persons having ordinary skill in the art to which the present invention pertains from the following description taken in conjunction with the accompanying drawings.

SUMMARY OF THE INVENTION

The present invention is an apparatus and method for the modification of viruses and bacteria in the body. The apparatus consists of a cuvette, an irradiation station, a peristaltic pump, and a bottle which are all systematically situated with respect to a housing. A plurality of power control switches controls the operation of the apparatus. This includes an on/off power switch, an on/off pump control, and a ultraviolet light control switch. A timer is provided to regulate the time period the cuvette is exposed to the ultraviolet radiation within the irradiation station. A cover is provided to enable the cuvette to be used and exposed to ultraviolet radiation within an enclosed environment.

BRIEF DESCRIPTION OF THE DRAWINGS

The Description of the Preferred Embodiment will be better understood with reference to the following figures.

DETAILED DESCRIPTION OF THE PREFERRED EMBODIMENT

Figure 1:
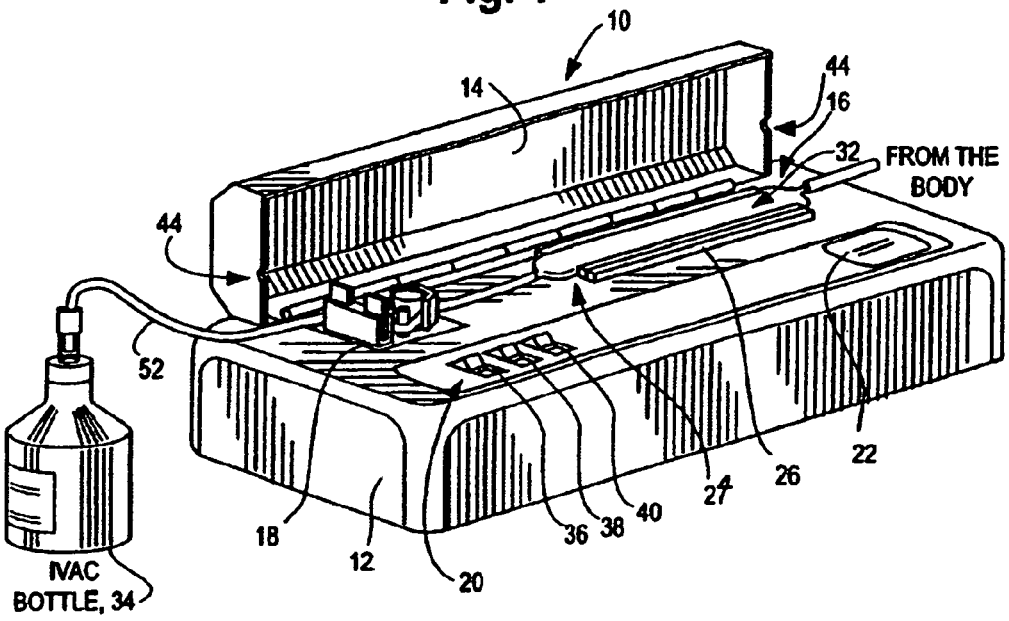
FIG. 1 is a perspective view of the irradiation apparatus of Applicant's invention for the eradication of viruses and bacteria within the body.

Turning first to FIG. 1, there is illustrated a blood irradiation apparatus 10. The blood irradiation apparatus 10 consists of a housing 12 and a cover 14. In the preferred embodiment, the housing 12 and the cover 14 are made from metal (e.g., similar to that used for storage cabinets). Alternatively, it is contemplated that the housing 12 and the cover 14 may be made of a durable plastic material. Situated along the exterior surface of the housing 12 is an irradiation station 16, a pump 18, a plurality of power control switches 20, and a timer 22. Situated at a position adjacent to the housing 12 is a bottle 34. Alternatively, any other sterilized bottle 34 may be used provided the pump 18 is used during the process as described later in the specification.

Figure 2:
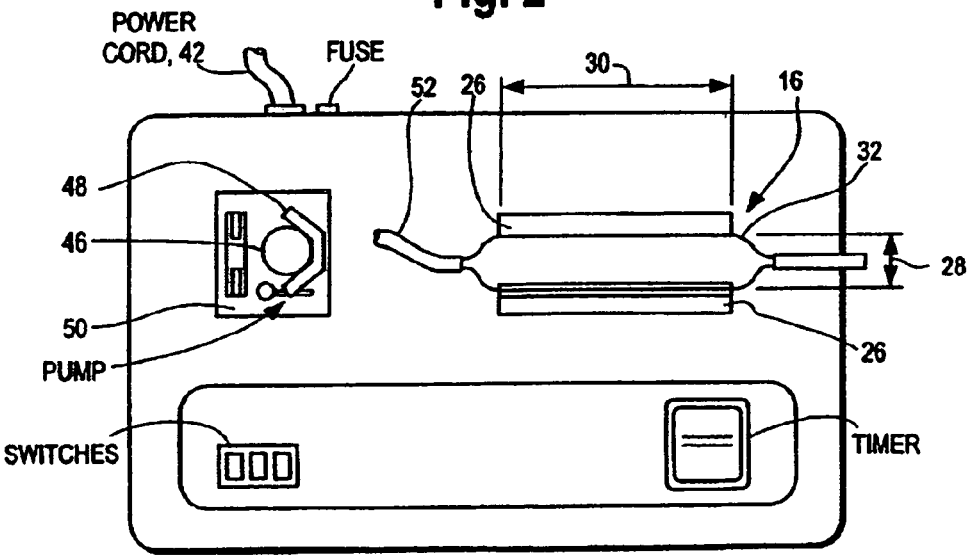
FIG. 2 is top planar view, with portions removed, illustrating the control features of the apparatus in relation to the cuvette.

The irradiation station 16 consists of a lens or faceplate 24 and brackets or sides 26. The faceplate 24 is a flat surface and is made of a quartz crystal material. The faceplate 24 has a width 28 (FIG. 2) and a length 30 (FIG. 2). In the preferred embodiment, the width 28 is approximately one and one-eighth of an inch (1⅛") and the length 30 is approximately five and one-quarter of an inch (5¼"). The purpose of the faceplate 24 is twofold: (1) to coact with the brackets or sides 26 to retain a cuvette 32 in an elongated, flat position, and (2) to facilitate the ultraviolet irradiation of the cuvette 32 as described in further detail herein and, in particular, with respect to FIG. 3.

In the preferred embodiment, the cuvette 32 is preferably made of a quartz crystal material and is placed within the irradiation station 16. Alternatively, it is contemplated that the cuvette 32 may be made of a durable plastic material. The cuvette 32 is preferably laid flat against the faceplate 24 and displaced evenly across the surface area of the faceplate 24. In this manner, the largest cross section of liquid or blood passing through the cuvette 32 is ultimately exposed to the ultraviolet light radiation. After the cuvette 32 is used for the treatment of fluid, the cuvette 32 can be disposed of and replaced with a new, unused cuvette 32. This effectively eliminates all chances of any kind of contamination in subsequent modalities or processes.

The pump 18 is preferably a peristaltic pump or the commonly referred to "paddle" pump. The pump 18 consists of a wheel 46 (FIG. 2), a jaw 48 (FIG. 2), and a securing means 50 (FIG. 2) for securing the jaw 48 in relation to the wheel 46. A conduit 52 extends from the cuvette 32 through the pump 18 and ends at the bottle 34. In use, the conduit 52 contains the matter such as liquid or blood from the body. While transporting the liquid or blood from the body through the blood irradiation apparatus 10, the conduit 52 is placed between the wheel 46 and the jaw 48. The pump 18, using the wheel 46 which has nubs (not illustrated) and which are equally spaced around the circumference of the wheel 46, creates wavelike contractions in the conduit 52 from the pressure of the nubs upon the conduit 52 (i.e., squeezing of the conduit 52) during rotation of the wheel 46. These wavelike contractions facilitate the transportation of the liquid or blood from the body and through the blood irradiation apparatus 10.

The plurality of power control switches 20 consists of an on/off power switch 36, an on/off pump control switch 38, and an ultraviolet light control switch 40. The on/off power switch 36 controls the electrical power of the blood irradiation apparatus 10. A power cord 42 (FIG. 2) provides continuous electrical power source to the blood irradiation apparatus 10. If the on/off power switch 36 is depressed to the off position, the blood irradiation apparatus 10 will not be energized and prohibited from operating. If the on/off power switch 36 is depressed to the on position, the electrical power supplied from the power cord 42 will permit the operation of the blood irradiation apparatus 10. The on/off power switch 36 and the power cord 42 is the means for energizing the fluid or blood irradiation apparatus 10. Likewise, the on/off pump control switch 38 operates in the same manner as the on/off power switch 36 except that the on/off pump control switch 38 controls the operation of the pump 18. The ultraviolet light control switch 40 also operates in the same manner as the on/off power switch 36 and the on/off pump control switch 38 by toggling between an "on" position and an "off" position. In the "on" position, the ultraviolet light control switch 40 enables the cuvette 32 to be irradiated with the ultraviolet light radiation. When the ultraviolet light control switch 40 is toggled back to the "off" position, the irradiation of the ultraviolet light on the cuvette 32 is terminated. In the preferred embodiment, the timer 22 provides the total amount of time that the cuvette 32 has been exposed to the ultraviolet light radiation or, in other words, allows the user to control or regulate the irradiation time of the liquid or blood. The plurality of power control switches 20 consisting of the on/off power switch 36, the on/off pump control switch 38, and the ultraviolet light control switch 40 is the means for controlling the operation of the fluid or blood irradiation apparatus 10.

The cover 14, during use and the modification process, is in the closed position to enclose the pump 18, the cuvette 32, and the irradiation station 16. The purpose of the cover 14 is to protect the attendant or others adjacent to the blood irradiation apparatus 10 from any harmful ultraviolet light radiation during the modality or process. The cover 14 contains apertures 44 which provide egress for the conduit 52 transporting the blood to and from the patient through the blood irradiation apparatus 10. When the cover 14 and/or the blood irradiation apparatus 10 are not being used, the cover 14 in placed in the open position to permit access to the pump 18 and the irradiation station 16 for purposes of servicing these components. For example, with the cover 14 in the open position, the cuvette 32 may be replaced within the irradiation station 16. The cover 14 is the means for enclosing the cuvette 32 and irradiation station 16 when the fluid or blood irradiation apparatus 10 is in use for minimizing the escape of ultraviolet light radiation.

Figure 3:
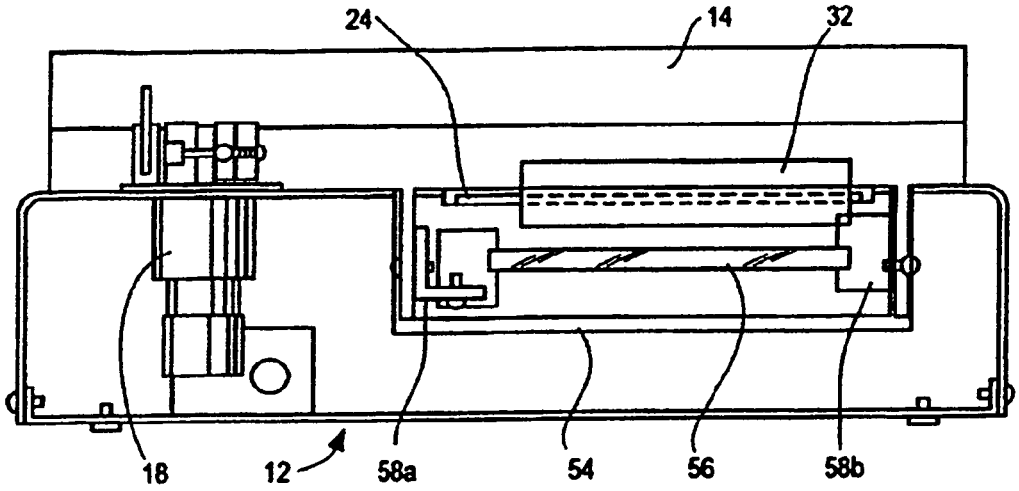
FIG. 3 is a side planar view, with portions removed, illustrating the ultra violet radiation of the cuvette.
Figure 4:
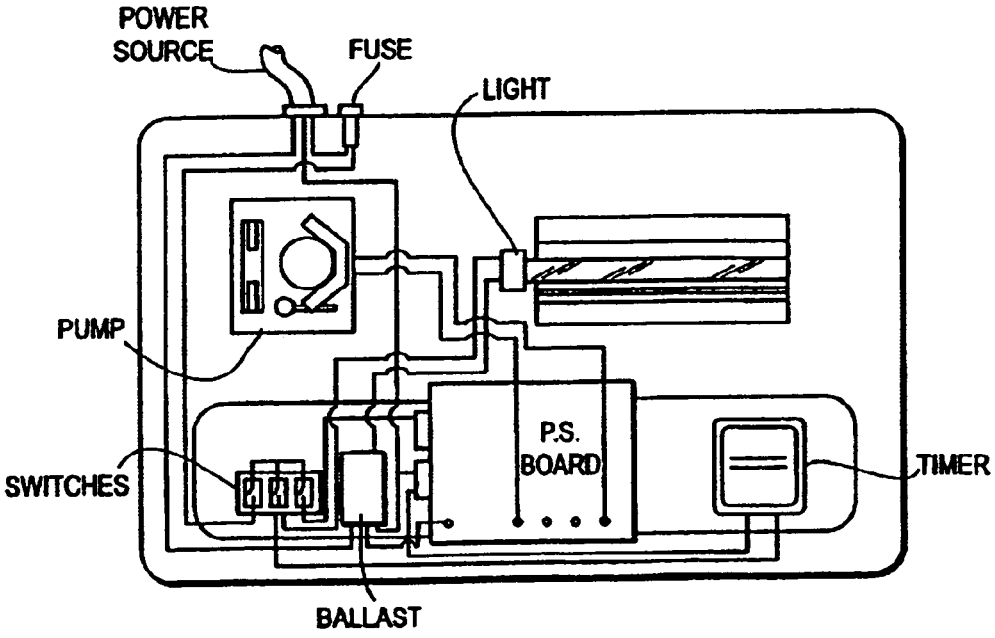
FIG. 4 is an electrical schematic diagram of the apparatus.

Turning to FIG. 3, the irradiation of the cuvette 32 is more clearly illustrated. Located within the housing 12 is a radiation box 54 and an ultraviolet light source 56. The ultraviolet light source 56 is held into position within the radiation box 54 by holding elements 58a and 58b. Preferably, the ultraviolet light source 56 is aligned parallel to and adjacent to the cuvette 32 to enable a consistent and uniform irradiation of blood when the blood irradiation apparatus 10 is in use. The ultraviolet light source 56 is calibrated to different light transmission band widths. For example, the ultraviolet light source 56 is capable of being calibrated in each of the UVA, UVB or UVC light band widths or between 40 to 400 nano meters. The blood irradiation apparatus 10 is more effective by using a pure ultraviolet light that is calibrated to the right frequencies needed to modify the viruses and/or bacteria. The timer 22 is beneficial here as it provides the total time that the ultraviolet light source 56 has been used. This information is useful as the ultraviolet light source 56 should be calibrated every 1000 hours and replaced every 8000 hours or sooner, if needed. In the preferred embodiment, the radiation box 54 is removable from the housing 12 to enable the ultraviolet light source 56 to be calibrated or replaced as desired.

In use, liquid or blood is withdrawn by venipuncture from the body through a conduit 52 and into an irradiation chamber or cuvette 32. Once within the cuvette 32, the liquid or blood is exposed to a controlled amount of ultraviolet light energy from the ultraviolet light source 56 within the radiation box 54 and through the faceplate 24. The amount of ultraviolet light energy is provided in the accepted therapeutic band in order to modify the virus or bacteria. The liquid or blood continues through to either the peristaltic pump 18 on the way to the bottle 34 or bypasses the peristaltic pump 18 and goes directly into the ivac bottle 34. The bottle 34 is the means for receiving the fluid transported and irradiated through the cuvette 32. If the liquid or blood is being transported from the body through the blood irradiation apparatus 10 by the pump 18, the liquid or blood will pass through the pump 18 in conduit 52 as it is the pump 18 which is artificially causing the transportation of the liquid or blood through the system. Alternatively, if the peristaltic pump 18 not being used, an ivac bottle 34 can be used as it provides its own vacuum to draw the blood from the body at a controlled rate. The peristaltic pump 18 or ivac bottle 34 is the means for drawing and transporting the fluid through the cuvette 32. This type of technique is also referred to as the Knott technique. Using the Knott technique, the liquid or blood will bypass the pump 18 and be transported directly into the bottle 34.

In the preferred embodiment, the amount of blood withdrawn from the body is approximately 1.5 cc of blood per pound of body weight with the total amount of blood per modality or process never exceeding 250 cc of blood. The reason is that if more than 250 cc of blood is removed from the body in one process, the blood remaining in the body would not be at an acceptable, healthy level for the patient. After the desired amount of blood is transported completely through the blood irradiation apparatus 10 and is contained within the bottle 34, the bottle 34 is then elevated into the air to a location above the blood irradiation apparatus 10. Once in this position, the bottle 34 is opened and the blood is permitted to drip from the bottle 34 to be transferred back through the blood irradiation apparatus 10 and returned to the body. Depending upon the amount of blood impacted and the desired retention time, the drip rate from the bottle 34 can be adjusted accordingly. The irradiated blood leaves the bottle 34 and returns through the cuvette 32 and the irradiation station 16 for a second time and is, once again, exposed or irradiated to a controlled amount of ultraviolet light energy from the ultraviolet light source 56 within the radiation box 54 and through the faceplate 24. The liquid or blood then continues back into the body through the same needle used for withdrawl. This entire process including the bottle 34 and the timer 22 is the means for returning the fluid back through the cuvette 32 from the bottle 34. This entire process is considered a single modality and is contained within a closed system that prohibits the introduction or potential for foreign objects or other contaminants to enter the system or adversely affect the procedure. An average procedure takes approximately one hour and patients can receive, at scheduled times, multiple procedures or as many procedures as it takes to positively impact the condition. The blood irradiation apparatus 10 is capable of modifying known viruses and bacterial diseases which includes but is not limited to septicemias, pneumonias, peritonitis, viral infections including acute and chronic hepatitis, atypical pneumonias, poliomyelitis, encephalitis, mumps, measles, mononucleosis, herpes. It is contemplated that the blood irradiation apparatus 10 has positive effects of the diseases known to man with little or no side effects. Although throughout this disclosure the term "blood" is used to designate the fluid passed through the apparatus, it is recognized that other body fluids can also be passed through the apparatus with the same results. Accordingly, the term "blood" is also meant to encompass any body fluids (i.e., human, animal, etc . . .) capable of being irradiated.

Thus, there has been provided a blood irradiation apparatus that effectively uses a closed system to modify viruses and bacteria in the body and provide a positive impact on the condition while further eliminating contamination from external sources. While the invention has been described in conjunction with a specific embodiment, it is evident that many alternatives, modifications and variations will be apparent to those skilled in the art in light of the foregoing description. Accordingly, it in intended to embrace all such alternatives, modifications and variations as fall within the spirit and scope of the appended claims.

What is claimed is:

1. A fluid irradiation apparatus for the modification of viruses and bacteria, comprising:

a housing having an exterior side and an interior side, the interior side further defining an opening;

an irradiation station affixed to the housing, the irradiation station having a faceplate mounted thereto;

a cuvette positioned across the faceplate and secured to the housing;

an ultraviolet light source mounted adjacent to the faceplate and the cuvette;

an ivac bottle for drawing and transporting fluid through the cuvette;

means for receiving the fluid transported and irradiated through the cuvette;

means for enclosing the cuvette and irradiation station when the fluid irradiation apparatus is in use for minimizing the escape of ultraviolet light radiation; and means for energizing the fluid irradiation apparatus.

2. The fluid irradiation apparatus of claim 1 wherein the faceplate and the cuvette are made of a quartz crystal material.

3. The fluid irradiation apparatus of claim 1 wherein the cuvette is made of a durable plastic material.

4. The fluid irradiation apparatus of claim 1 wherein the ultraviolet light source is calibrated to different light transmission band widths.

5. The fluid irradiation apparatus of claim 4 wherein the ultraviolet light source is calibrated between 40 and 400 nano meters.

6. The fluid irradiation apparatus of claim 1 wherein the means for receiving the fluid transported and irradiated through the cuvette is a bottle.

7. The fluid irradiation apparatus of claim 1 wherein the means for enclosing the cuvette and irradiation station when the fluid irradiation apparatus is in use is a cover.

8. The fluid irradiation apparatus of claim 1 and further comprising an on/off power switch, an on/off pump control switch, and an ultraviolet light control switch.

9. A fluid irradiation apparatus for the modification of viruses and bacteria contained in fluid, comprising:

a housing having an exterior side and an interior side, the exterior side further defining an aperture and the interior side further defining a hollow center;

a faceplate fitted within the aperture in the exterior side of the housing;

a cuvette positioned across substantially the surface area of the faceplate and aligned in a substantially parallel relationship with the faceplate;

an ultraviolet light source located within the opening of the interior side and positioned parallel to the faceplate and the cuvette;

a bottle for receiving the fluid transported through the cuvette;

means for transporting the fluid through the cuvette into the bottle;

means for returning the fluid back through the cuvette from the bottle;

whereby, the fluid transferred through the same cuvette is irradiated in at least two separate instances by the ultraviolet light source emitted through the faceplate.

10. The fluid irradiation apparatus of claim 9 and further comprising a means for drawing the fluid through the cuvette.

11. The fluid irradiation apparatus of claim 9 and further comprising a means for enclosing the cuvette when the fluid irradiation apparatus is in use.

12. The fluid irradiation apparatus of claim 9 and further comprising a means for controlling the operation of the fluid irradiation apparatus.

13. A method for modifying viruses and bacteria from fluid in the body, comprising the steps of:

(a) providing a fluid irradiation apparatus consisting of a housing and an irradiation station in the housing;

(b) removing fluid from the body and depositing the fluid into a conduit;

(c) transporting the removed fluid from the body along the conduit and into a cuvette;

(d) irradiating the removed fluid at the irradiation station within the cuvette by an ultraviolet light source;

(e) transporting the irradiated fluid from the cuvette along the conduit and depositing the irradiated fluid into a container;

(f) removing the irradiated fluid from the container and depositing the fluid back into the conduit;

(g) transporting the irradiated fluid back through the same conduit and back into the same cuvette;

(h) irradiating the irradiated fluid within the cuvette by the ultraviolet light source to produce a second irradiated fluid;

(i) transporting the second irradiated fluid back through the same conduit from the cuvette;

(j) returning the second irradiated fluid into the body.

14. The method of claim 13 and the additional step of directing ultraviolet radiation from the ultraviolet light source at the cuvette.

15. A method for modifying viruses and bacteria from fluid in the body, comprising the steps of:

(a) transporting fluid through a conduit into a cuvette;

(b) providing an ultraviolet light source at the cuvette;

(c) irradiating the fluid in the cuvette as it passes the ultraviolet light source to produce a first irradiated fluid;

(d) reversing the directional flow of the fluid to pass back through the same cuvette; and (e) irradiating the first irradiated fluid as it passes the ultraviolet light source a second time to produce a second irradiated fluid.

* * * * *